(12) United States Patent  
Aeschlimann et al.

(10) Patent No.: US 8,670,836 B2
(45) Date of Patent: Mar. 11, 2014

(54) MEDICAL INFUSION PUMP WITH POWER SOURCE VOLTAGE LOGGING AND METHOD FOR LOGGING A POWER SOURCE VOLTAGE IN A MEDICAL INFUSION PUMP

(75) Inventors: Reto Aeschlimann, Aefligen (CH); Thomas Rufer, Ostermundigen (CH)

(73) Assignee: Roche Diagnostics International AG, Rotkreuz (CH)

( * ) Notice: Subject to any disclaimer, the term of this patent is extended or adjusted under 35 U.S.C. 154(b) by 0 days.

(21) Appl. No.: 13/570,696

(22) Filed: Aug. 9, 2012

(65) Prior Publication Data

US 2012/0302988 A1 Nov. 29, 2012

Related U.S. Application Data

(63) Continuation of application No. 12/877,582, filed on Sep. 8, 2010, now Pat. No. 8,262,617.

(30) Foreign Application Priority Data

Sep. 10, 2009 (EP) .................................... 09169936

(51) Int. Cl.
*A61N 1/00* (2006.01)
(52) U.S. Cl.
USPC ............................... 607/60; 604/151; 307/64

(58) Field of Classification Search
USPC ........ 607/60; 604/151; 307/64; 323/299, 303; 702/63–64
See application file for complete search history.

(56) References Cited

U.S. PATENT DOCUMENTS

| | | | |
|---|---|---|---|
| 5,321,392 A | 6/1994 | Skakoon et al. | |
| 5,764,034 A | 6/1998 | Bowman et al. | |
| 5,847,587 A * | 12/1998 | Chen et al. | 327/143 |
| 5,876,423 A | 3/1999 | Braun | |
| 6,494,827 B1 | 12/2002 | Matsumoto et al. | |
| 2002/0065454 A1 | 5/2002 | Lebel et al. | |
| 2003/0033550 A1* | 2/2003 | Kuiawa et al. | 713/340 |
| 2006/0271807 A1* | 11/2006 | Suzuki et al. | 713/600 |
| 2007/0040449 A1 | 2/2007 | Spurlin et al. | |
| 2007/0293914 A1 | 12/2007 | Woods et al. | |
| 2009/0108808 A1* | 4/2009 | He et al. | 320/134 |
| 2009/0190402 A1* | 7/2009 | Hsu et al. | 365/185.08 |

* cited by examiner

*Primary Examiner* — Quynh-Nhu H Vu
(74) *Attorney, Agent, or Firm* — Dinsmore & Shohl LLP

(57) ABSTRACT

A medical infusion pump and a method for logging a power source voltage of a medical infusion pump are disclosed. The medical pump may include a power source, a processor, and a voltage supervisor which responds if a voltage (VDD) drops to a response voltage level which is above a reset voltage level of the processor. When the voltage supervisor responds, the processor start logging the voltage (Vbat) of the power source in a memory, thus generating a voltage log. The memory maintains the logged data when the power supply by the power source is interrupted, thus enabling retrospective analysis of the voltage log.

20 Claims, 5 Drawing Sheets

MEDICAL INFUSION PUMP WITH POWER SOURCE VOLTAGE LOGGING AND METHOD FOR LOGGING A POWER SOURCE VOLTAGE IN A MEDICAL INFUSION PUMP

CROSS-REFERENCE TO RELATED APPLICATIONS

This application is a continuation of U.S. patent application Ser. No. 12/877,582 filed on Sep. 8, 2010, now U.S. Pat. No. 8,262,617 and which claims priority to European Patent Application No. EP 09 169 936.3 filed on Sep. 10, 2009.

TECHNICAL FIELD

The present disclosure relates to a medical infusion pump and in particular, to an ambulatory medical infusion pump and a method for logging a power source voltage of a power supply provided by a power source in the medical infusion pump. Such infusion pumps can be, for example, insulin pumps, in particular worn by a person continuously night and day.

BACKGROUND

Medical infusion pumps may be designed to be carried by a user, to a large extent, continuously and concealed from view. In some embodiments, the medical infusion pump may have a size of about a cigarette packet or less and be designed to be carried in a belt holster, in a trouser's pocket, in a necklace-like way, or the like. In addition, such medical infusion pumps are designed to be coupled with a subcutaneous infusion cannula via a tubing of, e.g., 0.3 m to 1.5 m length. In other embodiments, a medical infusion pump may include a subcutaneous infusion cannula and be adhesively attached directly to the skin of a patient at the infusion site.

Some medical infusion pumps may be designed to infuse medicine in accordance with a quasi-continuous and time-variable infusion profile. Such infusion pumps may be used, for example in the therapy of diabetes mellitus by quasi-continuous subcutaneous insulin infusion, CSII. In CSII therapy, insulin is subcutaneously infused into a diabetic's body in accordance with the diabetic's personal and time-varying basal insulin demands. Such an infusion pump may further be designed to infuse additional medicine insulin boli on demand, for example insulin boli to cover the intake of carbohydrate-comprising meals.

Medical devices like medical infusion pumps are typically powered by an electrical power source, typically a rechargeable or non-rechargeable battery, such as a common AA or AAA cell or a special-purpose power pack. The medical infusion pump typically comprises a housing with a user-accessible compartment or interface for holding or attaching the power source in a replaceable way. Those devices typically further comprise at least one processor, for example in form of an ASIC or microcontroller, which controls the device operation.

A failure occurs if the voltage provided by the power source to the medical device or specific components within the medical device drops to a critical value. The critical value is also called a reset voltage level because further operation is not possible and a reset of the medical device or a specific component within the medical device, in particular the processor, is performed at this voltage level. This results in the device stopping, at least temporarily, intended operations. For a medical infusion pump, this means typically terminating infusion. In some cases, the user, for example a diabetic, may not even become immediately aware of this potentially dangerous situation.

For liability reasons as well as for general failure and complaint-analysis-purposes, it is of considerable value to know if the reason for an interruption of the power supply was either a misuse of the device by the user such as, for example, removing the power source during normal operation or dropping of the device, or a problem within the medical device such as, for example, within the power source itself.

SUMMARY

In one embodiment, a medical infusion pump is disclosed which comprises a processor, a power source having a power source voltage (Vbat) powering the processor, and a voltage supervisor which monitors a processor supply voltage (VDD) and responds if the processor supply voltage (VDD) drops to a predetermined response voltage level which is above a reset voltage level of the processor. When the voltage supervisor responds, the processor starts logging the power source voltage (Vbat) in a memory to generate a voltage log. The memory is designed to maintain the logged data when the power supply by the power source is interrupted to enable retrospective analysis of the voltage log.

In another embodiment, a method for logging a power source voltage (Vbat) of a power source in a medical infusion pump is disclosed. The medical infusion pump comprises a processor, and the power source powers the processor with the power source voltage (Vbat). The method comprises: detecting if the processor supply voltage drops to a predetermined response voltage level which is higher than a reset voltage level of the processor; starting to log the voltage (Vbat) of the power source when the processor supply voltage (VDD) has dropped to the predetermined voltage level to generate a voltage log; and maintaining the logged data when the power supply by the power source is interrupted to enable a retrospective analysis of the voltage log.

These and other advantages and novel features of the invention will become apparent from the following detailed description of the invention when considered in conjunction with the drawings.

DETAILED DESCRIPTION

Figure 1:
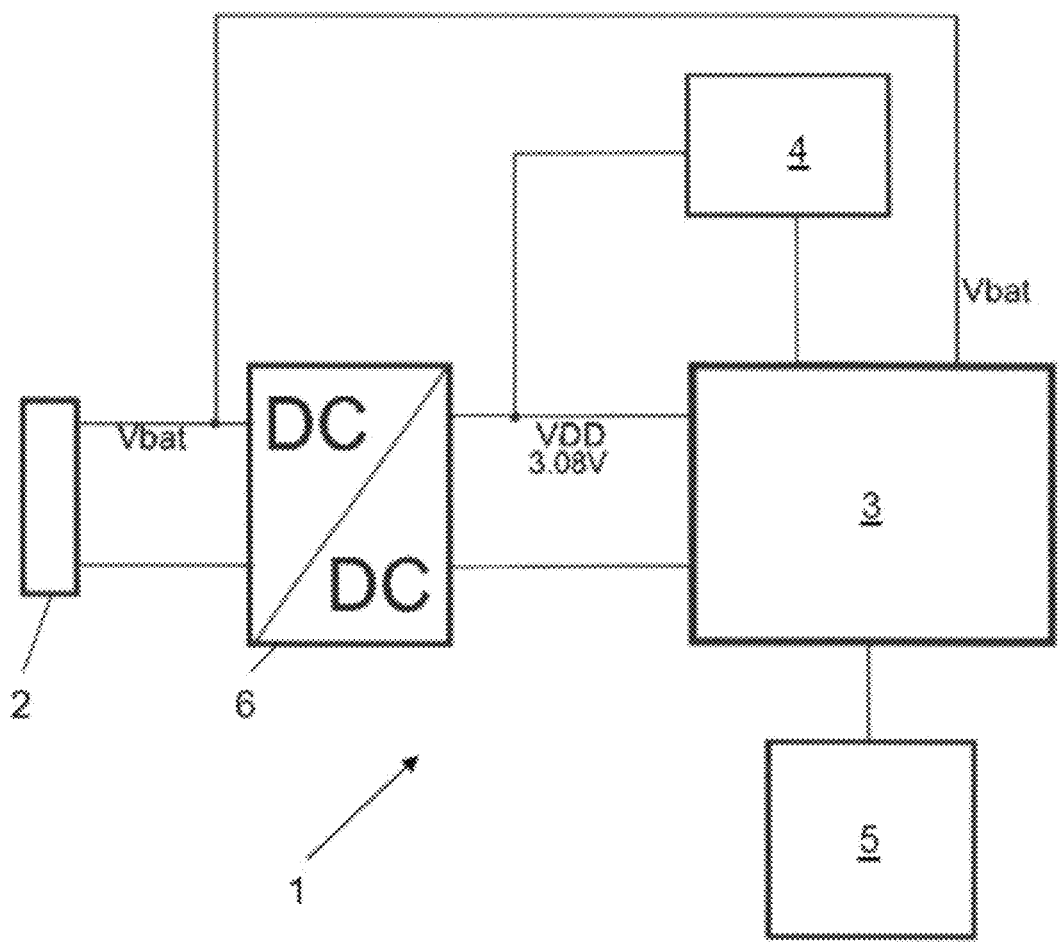
FIG. 1 depicts a schematic block diagram of a medical infusion pump according to an illustrated embodiment.

Medical infusion pumps as well as corresponding methods that enable analyzing, retrospectively, a reason for a power supply interruption are disclosed. For example, the reason for such a power supply interruption may be determined by analyzing the power source voltage as a function of time at and shortly before the interruption. It is therefore advantageous in one embodiment to provide a medical infusion pump that includes features for supporting a technical expert in analyzing the cause of an interruption of a power supply by providing suited operational data as well as methods for collecting such data.

In some embodiments of medical infusion pumps and methods in accordance with the present disclosure, determining the cause of a power supply interruption is carried out, at least partly, by the infusion pump itself. In other embodiments, the device provides the data that allow a technical expert to carry out the analysis.

In the following discussion, typical scenarios for a power supply interruption are discussed in some more detail. If the power source is suddenly removed, the power source voltage rapidly falls to zero or near zero and remains there. The voltage may fall to near zero, instead of zero, if there is a capacitor present in parallel to the battery. The residual voltage level, which falls under the term "near zero", can have levels, for example, of up to 0.5 volts.

A sudden interruption of the power supply may occur in different situations. The infusion pump may include one or more contact springs for electrically connecting the power source in a releasable way. If the medical device is dropped, such that the contacts temporarily detach, there is a steep notch in the power source voltage to zero or near zero for a short period of time, thereby resulting in a reset of the processor, followed by a subsequent power-up.

The same effect may occur in case of a mechanical shock. For example, diabetics are known to push occasionally an insulin pump onto a table in order to remove air bubbles from an insulin cartridge in a cartridge compartment of the pump. In the following, however, the term "dropping" as used herein generally covers mechanical shocks that have substantially the same effect as the medical infusion pump being dropped.

In some cases, a power source is removed by the user during normal operation of the device. Here, a power-up only occurs when the same or a new battery is connected.

The term "normal operation" as used herein refers to an operational mode where the medical infusion pump operates as intended. An insulin pump, for example, may infuse insulin in a quasi-continuous way as described above in a normal operation mode.

For example, the follow two events indicate a misuse or mishandling of the device by the user. At the time the processor supply voltage reaches the reset voltage level, the power source voltage is either still zero (or close to zero) in the case of a removed power source or may have recovered in the case of a dropped device. From the profile of the power source voltage, both events can therefore be distinguished.

A different situation occurs in cases where the power source, in particular a battery, is defective, weak or unsuited. This may cause a drop in the power source voltage, which, however, is generally not as steep and not as deep as in cases where the power source is removed or temporarily disconnected. This means that the profile of the power source voltage is different. In particular, at the time when the processor supply voltage reaches the reset voltage level, the power source voltage is higher than in the first two events. Therefore, the cause of the interruption of the power supply to the processor can be determined from the logged power-source voltage profile, in particular from the voltage value or level at the time when the processor supply voltage reached the reset voltage level.

A further example for a device-internal error is a loose contact to the power supply which may result in a number of repeated interruptions of the power supply.

Here and in the following, a power source voltage that is logged when the processor supply voltage drops to the reset voltage level is to be understood in the sense of the last logged value before the processor stops logging because the processor supply voltage has reached or fallen below the reset voltage level. In addition, it should be noted that a dropping voltage does not necessary stop dropping at a specified level. "Dropping to a level" therefore has to be understood in the sense of assuming and typically falling below that level.

As will be discussed below in more detail, conclusions can also be drawn from the relative times of the battery source voltage dropping to the predetermined voltage level, the processor supply voltage dropping to the reset voltage level, and the processor being subsequently powered up again.

U.S. Pat. No. 5,764,034 discloses a battery gauge for a battery operated infusion pump as well as formulas for calculating a remaining battery lifetime based on six stored voltage values, each of which represents an average of several voltage samples.

Us 2007/0293914 A1 discloses a system and a corresponding method for determining the status of a rechargeable battery in an implantable medical device with the battery voltage being measured with a predetermined time interval, e.g. four hours and e.g. every 10 sec. after the battery voltage has falling below a specified minimum level.

A medical infusion pump according to an embodiment of the present disclosure may comprise a power source, a processor and a voltage supervisor with the power source powering the processor. The voltage supervisor is configured to monitor the processor supply voltage and the voltage supervisor is further configured to respond if this voltage drops to a predetermined response voltage level above the reset voltage level of the processor. The response voltage level may be adaptive and be selected, for example, in dependence of the power source type, the temperature, and further factors.

The processor can, as generally known in the art, be any central processing unit (CPU) or any microprocessor, microcontroller or ASIC, or combination of those, including discrete circuitry. The battery can be a single-use battery or rechargeable battery, for example.

As used herein, the phase "responding of the supervisor" means that the supervisor provides an output signal which indicates that the voltage has dropped to the response voltage level. Such a supervisor continuously compares the processor supply voltage with an internal reference level. Continuous operation is necessary because a power supply interruption caused, e.g., by a drop, may occur at any time.

As used herein, the term "reset" means a process where the processor terminates operation when the processor supply voltage reaches and falls below the reset voltage.

The processor stays non-operable as long as the processor supply voltage is either not present or below the reset voltage level. As the processor supply voltage passes the reset voltage level and exceeds it, the processor starts operating again in a pre-defined reset state. The latter phase is also referred to as "powering up" the processor.

The voltage supervisor may be external to the processor, an internal component of the processor or a functionality of the processor, for example, using an internal A/D (analog-to-digital) converter and logic circuitry, or any combination of those.

The processor is configured to start logging the voltage of the power source to a memory, thus creating voltage log as profile of the voltage over time, when the voltage supervisor responds. The logging is carried out with a sufficiently high sampling rate to ensure that a number of values are logged before the voltage drops to the reset voltage level and the processor stops operation. It is typically in the range of some kHz. The memory is favorably a non-volatile memory RAM (random access memory) that is designed to maintain stored data in the absence of a supply voltage. In principle, however, it may also be a volatile memory which is powered by an independent power supply. Because the memory maintains the data (i.e., logged data), retrospective analysis of the power log is enabled. The memory is typically also powered by the power source.

The logged data can be analyzed using an external device which is configured to receive the logged data from the medical infusion pump to determine the cause of an interruption of the power supply to the processor from the logged power source voltage. After transmitting the data to the external device, they may be analyzed, evaluated and potentially stored, e.g., for liability reasons, by a medical expert and/or by automated system.

For transmitting the logged data to the external device, such as a standard personal computer or a dedicated diagnosis device, a data interface, in particular a wireless data interface such as an IR (infrared) interface or RF (radio frequency) interface, e.g., based on the Bluetooth standard, may be present in the infusion device. Such a data interface may also be used for additional purposes, for exampling remote controlling the infusion pump during normal operation.

A technical expert can accordingly evaluate the logged power source voltage profile shortly before the reset and determine the course of the interruption from the log by evaluating characteristic data, such as the power source voltage when the processor supply voltage reaches the reset voltage level, with corresponding characteristic data for different courses of the interruption. Alternatively or additionally, the voltage log itself, that is, the power source voltage as a function of time, is compared with corresponding characteristic reference profiles manually by visual and/or automated comparison.

In some embodiments, this evaluation or analysis is, completely or partly, carried out by the infusion pump itself and the result is favorably displayed and stored. Since the stored voltage log is maintained during the power supply interruption, this analysis or evaluation can be, manually or automatically, carried out retrospectively, for example after the next following power-up.

In order to allow retrospective evaluation, the memory of the medical infusion pump may be configured to store permanently the voltage log and/or characteristic data that are extracted or determined from the voltage log. "Permanently storing" as used herein refers to the stored data being maintained during all situations that may typically occur during usage of the pump, including replacing the power source or removing the power source for an extended time periods of, e.g., several weeks or months. It may, however, be possible for such data to be cleared, for example by a technical expert, typically following transferring the data to an external device as described above and/or analyzing the cause of the power supply interruption.

In the following, it is mostly assumed that the voltage log is stored for later evaluation. As will become more readily apparent as the description proceeds, however, it may be sufficient to store only a number of characteristic data that is extracted or computed from the voltage log and reflects the cause of a power supply interruption. While being associated with a loss of information, it is favorable with respect to memory demand.

The response voltage level of the voltage supervisor is above the reset voltage level of the processor. In the time span between those two events, the processor is able to log the power source voltage. In general, the response voltage level is below a minimum typical voltage level which may occur during normal operation of the device due to general variation, temperature effects, etc., but above the reset voltage level of the processor. However, a voltage level below a response voltage level, but still above the reset voltage level, may occur sporadically during normal operation, for example in a situation where an extraordinarily high current is drawn by the infusion pump and the temperature is low. In particular, the voltage supervisor may respond at a level that is about 0.1 volts to 0.2 volts above the reset voltage level. As will be discussed below, the processor supply voltage is typically not identical to the power source voltage.

In some embodiments, the infusion device is configured to test, during normal operation, the battery voltage with a fixed or variable testing interval and to provide a warning if the power source approaches the end of its lifetime. Those tests are carried out independently of the operation of the voltage supervisor. One or multiple voltage levels may be provided with different voltage level. At the lowest of such level, operation of the pump may be automatically terminated in order to prevent malfunction resulting from an expired power source. The predefined voltage is typically selected (however, not essentially) somewhat below all of those voltage levels such that the power source can be replaced without the voltage supervisor responding. Testing of the battery during regular operation may also be carried out via further advanced methods, such as fuel gauging.

As an option, there is a voltage converter provided between the power source and the processor. This voltage converter converts the power source voltage, which might be, for example between about 1.2 volts to about 1.5 volts, to the operating voltage of the processor, which might be, for example about 3 volts. In one embodiment, the voltage converter is a step-up DC-DC-converter. As an option, the voltage converter may contain a power buffer, such as a capacitor, for stabilizing its output voltage. The output voltage of such a DC-DC converter is constant for a given input voltage range, largely independent of the drawn current, but decreases if the input voltage of the converter falls below the lower limit of that range. Additionally or alternatively to such a converter, further voltage stabilization circuitry may be present. In embodiments where a voltage converter is present and the processor supply voltage is accordingly different from the power source voltage, the processor supply voltage may be logged in addition to the power source voltage to provide additional information for the analysis. It should further be noted that in embodiments where no voltage converter or further voltage stabilization circuitry is present, the power source voltage may be identical to the processor supply voltage.

In some embodiments, the voltage supervisor is connected to an interrupt input port of the processor. In such a configuration, the processor is automatically aware that the processor supply voltage has dropped to the response voltage level without the need to sample actively the input to which the voltage supervisor is connected. Active sampling by the processor is less favorable with respect to energy consumption since the processor is typically in a low-power mode most of the time but has to be activated, that is, switched into an operational mode, for logging the power source voltage. However, it reacts on signals at an interrupt port also in the low-energy mode.

In some embodiments, the medical infusion pump is designed to infuse medicine in accordance with a quasi-continuous and time-variable infusion profile. Such a design is favorable, for example, for CSII therapy as discussed above. The infusion profile may be pre-programmed or may be adaptive, e.g., in dependence of a blood glucose level of the user.

In some of those embodiments, the processor is configured to generally operate in a low-power mode and to change into an operational mode periodically for controlling a pump unit of the medical infusion pump to infuse an amount of medicine, thus generating the time-variable infusion profile, and is further configured to change into an operational mode upon the voltage supervisor responding. An operational mode is a mode where the processor operates according to and carries out a software or firmware program code of the infusion pump.

Operating the processor in a low-power mode or a sleep mode most of the time is favorable with respect to energy consumption since a typical processor or microcontroller consumes, in a low power or sleep mode, only a fraction of the energy that is consumed during a normal operation mode. In a low-power or sleep mode, the operation of only some of the functional components, in particular timers, counters and the response to signals at interrupt ports, is maintained. The time period between infusions is typically in a range of some minutes, for example, about 1 min to about 30 min, such as about 3 min. The processor may further change into an operational mode if a typically present user interface of the infusion pump is operated such as, for example, for communicating with external devices such as a remote controller via data interface, for safety and integrity checks, including checking the status of sensors, such as an occlusion sensor, or the like.

Through a changing into an operational mode in the case of the voltage supervisor responding, e.g., via an interrupt port as discussed above, the processor may at any time start logging the power source voltage where required, without consuming additional energy otherwise. In this context, it should be noted that an interruption of the power supply may suddenly occur at any time and for example in the case of the device being dropped, may be present only for a short time in the milliseconds range until it is powered-up again. In contrast to the processor when being in an operational mode, the power consumption of the voltage supervisor is negligible, such that it may operate continuously.

Logging the power source voltage is typically performed with an A/D converter with an input that is connected to the power source. The converter may be part of the processor or may be separate. If the analog-to-digital converter has low power consumption, for example in the range of or even below 0.1 mW, it may be operated continuously without significantly reducing the lifetime of the power source. The commercially available converters AD7466 by Analog Devices, Norwood Mass., USA, for example, has a power consumption of 0.12 mW, while the ADS7822 by Texas Instruments, Dallas Tex., USA, has a power consumption of 0.06 mW, either of which may, for example be used. In embodiments where the analog-digital-converter operates continuously, it may be directly used to detect the power source voltage falling below the response voltage level by continuously comparing its output with a reference value that represents the response voltage level. Alternatively, the A/D converter may be configured to start operating upon the voltage supervisor responding. In such an embodiment, the voltage supervisor may be realized as functionally separate voltage comparator.

In one embodiment, the processor is configured to log the power source voltage, upon a response of the voltage supervisor, until the processor supply voltage drops to the reset voltage level, such that the processor is reset as described above. The processor supply voltage dropping to the reset voltage level terminates the voltage logging by the processor. The power source voltage shortly prior the time the processor supply voltage reaching the reset voltage level is indicative of the event that caused the power supply interruption as described above.

Occasionally, it may occur that the processor supply voltage falls below the response voltage level to a minimum level that is close to the reset voltage level without, however, actually reaching the reset voltage level, but recovering before that level. This may be the case, for example, for a generally weak or largely empty but still operating battery if an exceptionally high power is drawn by the pump for a short time period or the infusion pump is dropped with the power source voltage recovering quickly. In such a situation, operation of the infusion pump is not effected.

The processor may therefore be configured to log, upon a response of the voltage supervisor, the power source voltage until the course of the power source voltage indicates that the processor supply voltage will not drop to the reset voltage level and subsequently stop logging. For this purpose, a predetermined stopping voltage level may be provided and logging may be stopped if the power source voltage rises above the stopping voltage level. This stopping voltage level may be the same level as the response voltage level of the voltage supervisor or may be different, in particular somewhat higher. Alternatively or additionally to stopping the logging if the power source voltages rises to or above a predefined stopping voltage level, logging may be automatically stopped a predefined time span after starting the logging without the processor supply voltage having fallen below the reset voltage level. This time span should be longer than the maximum time of a power supply interruption that may result from the device being dropped. The time span may, for example, be somewhere in the range of about 0.5 sec. to about 30 sec, and in one embodiment, about 1 sec. In dependence of the real-time computing capabilities of the processor while logging, further more advanced, approaches, such as evaluating a time-derivative of the power source voltage, may also be employed.

If the voltage supervisor is designed to provide a response continuously as long as the processor supply voltage is below the response voltage level, the processor may be configured to log the power source voltage until the voltage supervisor stops responding. Alternatively, a response of the voltage supervisor may be used only to start the logging, while the logged power source voltage itself is evaluated to stop the logging as described above. For those embodiments, the voltage supervisor may respond only short, for example by a pulse, upon the processor supply voltage dropping to the response voltage level.

For embodiments that allow logging such events, a short-term power supply interruption, for example caused by dropping the medical device, can be detected even if the processor supply voltage does not drop to the reset voltage level.

In case of an event where the reset voltage level is not fallen below, the processor may be configured to clear the voltage log after logging is stopped, since operation of the infusion pump was not affected. The event, however, may also be stored as "nearly interruption" of the power supply.

In embodiments where infusion pump is designed to automatically stop logging, the predetermined voltage level can be set conservatively, that is, comparatively high. In this case, the battery source voltage may occasionally be logged without being required. Setting the response voltage level too high, resulting in frequent responses of the voltage supervisor, should be avoided for energy consumption reasons.

As an option, the processor is configured to perform alternative logging of power source voltage values to different memories during the same logging procedure. This has the advantage that the voltage levels stored in one memory are not affected when the processor is reset during storing voltage levels to the other memory. In addition, each memory contains a reduced amount of data which can be sufficient for evaluating the cause of the power supply interruption in case the data stored in the other memory are corrupted. The different memories can be either different physical memories or different areas of the same physical memory. In the present disclosure, the term "memory" is generally used even though it may be a combination of memories, as explained.

The memory for voltage logs may be separate or integral with a general device history memory that is typically present and stores a device history. The device history comprises data with respect to various advents, such as medicine infusion, the occurrence of errors or hazards, the results of device self-checks, and the like. The memory in which the device history is stored is generally also a non-volatile memory and/or separately buffered.

In a preferred embodiment, the medical infusion pump comprises a clock circuit, which preferably continues running even if the power supply is interrupted by a separate power supply or a power supply buffer. The clock circuit can physically be a part of the processor or can be a separate unit.

In a preferred embodiment, the processor is configured to log a timestamp together with the power source voltage. The timestamp can be retrieved from the clock circuit. Dropping the medical device, which leads to a short-term interruption of the power source, basically has the same effect on the logged voltage as removing the power source. However, after an interruption caused by dropping the device, the power supply is interrupted for a period much shorter than when the power source is removed and re-inserted or replaced by the user. Therefore, by analyzing the timestamps of the logged power source voltage values as compared to the time at which the processor is subsequently powered up again, a drop of the device can be distinguished from removal of the power source. The time at which the processor is powered up again can also be retrieved from the clock circuit and stored in the device history, favorably with a corresponding event marker.

The term "timestamp" may and typically does include time of day information and potentially date information also that is typically provided by the clock circuit. The timestamps, may, however, also provide relative times, starting, for example, with zero at the point in time the voltage supervisor responds.

The processor may favorably be configured to store a timestamp and/or an event marker, the event marker being indicative for a preceding power supply interruption, in history of the medical infusion pump when being powered up again subsequently to a power source interruption.

The memory in which the log is stored may be suited for storing a single voltage log. For such embodiments, a stored log is favorably overwritten by a newer log if the voltage supervisor responds. While not all past events may be stored for later evaluation in this case, this type of embodiment enables analyzing the last log if the infusion pump is analyzed by a technical expert, for example if a user complaint results from a power supply interruption or if the infusion pump has to be analyzed because medical complications for the user occurred which may be related to the infusion device. The memory demand for storing a single voltage log is moderate.

Alternatively, the memory may be designed to store a number of, for example, 2, 5, 10, or 100 logs independently. For such embodiments, a number of logs can be analyzed for a given pump, for example if a pump is returned to the manufacturer or distributor at the end of its lifetime or for general maintenance. In the rare case where sufficient memory is not available for storing the logs, older logs may be replaced by newer logs, for example according to the last-in-last-out principle.

The infusion pump may be designed to permanently store complete voltage logs, thus allowing analyzing of the power source voltage as a function of time for a past event where the voltage supervisor responded. If no timestamps are stored, the generally known sampling frequency may be used to reconstruct the voltage as a function of time.

Alternatively to storing complete voltage logs, only characteristic data that are extracted or computed from the log, such as the power source voltage at the time the voltage supervisor starts responding and/or at the time the processor supply voltage falls below the reset voltage level, may be permanently stored for the evaluation, and favorably in some embodiments with a time stamp. In a variant, the complete log is stored in cases where the processor supply voltage has actually fallen below the reset voltage level, while only characteristic values and/or a message are stored in the case of "nearly interruptions" as explained above.

In a further variant, logging is only performed at those points in time where the processor supply voltage drops to the response voltage level and to the reset voltage level, respectively. Since those voltage levels are known in advance, the voltage values do not need to be stored but is generally sufficient to store the corresponding timestamps. For those embodiments, a normal A/D converter may not be required for the logging. Instead, dedicated voltage supervisors or voltage comparators for the response voltage level and the reset voltage level are sufficient.

It should be noted that in embodiments where only a number of extracted or computed data is stored rather than complete logs, the corresponding computational steps of data extraction or derivation do not have to be carried out in real time when an interruption of the power supply occurs, but may be carried out later on, for example after the following power-up of the processor.

Since the processor stops operation immediately or soon after the processor supply voltage dropping to the reset voltage level, the computational steps for extracting or deriving characteristic data typically cannot be carried out in real-time.

In some embodiments, the medical infusion pump is configured to be operated in a special operation mode where monitoring of the processor supply voltage is disabled or a voltage log that is generated with the ambulatory infusion device being in the special operation mode is subsequently cleared. Such a special operation mode may be either a stop mode or a maintenance mode selected by the user, for example, for replacing the energy storage as will be described below. This special operation mode is favorably an operation mode in which no infusion is carried out. Alternative, however, the pump may be designed to allow battery replacement during normal operations and bridges the power supply interruption by an internal buffer in this case.

The present disclosure also relates to a method for logging a power source voltage of a power source in a medical infusion pump, the medical infusion pump comprising a processor. The method may include the acts of detecting if the processor supply voltage drops to a predetermined response voltage level which is higher than the reset voltage level of the processor, and starting to log the voltage of the power source when the processor supply voltage has dropped to the response voltage level, thus generating a voltage log. The method may further include maintaining the logged data when the power supply by the power source is interrupted.

Details of the effects of this method and its advantages as well as of the response voltage level, the reset voltage level and ways for determining the cause of the power supply interruption from the logged data have already been explained above with reference to the medical infusion pump and are therefore omitted.

Embodiments of a medical infusion pump in accordance with the present disclosure may especially carry out embodiments of a logging method in accordance with the present disclosure. Therefore, aspects and embodiments of a medical infusion pump as disclosed above and below simultaneously detail embodiments of a corresponding logging method and vice versa.

Some or all features of different embodiments described above can be combined to new embodiments which are also covered by the present disclosure. In addition, the principles of the present disclosure can also be applied to all kinds of medical or non-medical devices with a power source, and not just to medical infusion pumps.

It is to be appreciated that the various embodiments of the present disclosure are also of particular use for retrospectively determining a cause of a power supply interruption in a device, such as a portable or handheld (electronic or electrical) device. In one particular embodiment, a mishandling or misuse of the device by a device user may be distinguished from technical reasons for the interruption, such as a device defect or a weak battery.

The following description and the annexed drawings set forth in detail certain illustrative aspects of the subject invention. These aspects are indicative, however, of but a few of the various ways in which the principles of the subject invention may be implemented.

FIG. 1 shows a schematic block diagram of a medical infusion pump 1, comprising a battery 2 as power source, a processor 3, a voltage supervisor 4, a memory 5 and a voltage converter 6. The battery 2 is connected electrically to the voltage converter 6. In one embodiment, the voltage converter 6 may be a DC-DC step-up converter which converts the output voltage of the battery 2 to the operating voltage of the processor 3. In one embodiment, the output voltage is between about 1.2 volts to about 1.5 volts, and the operating voltage of the processor 3 in one exemplary embodiment is about 3.08 volts. The output voltage or source voltage of the battery 2 is called Vbat, the output voltage of the voltage converter 6, which is the input and supply voltage of the processor 3, is called VDD. In the present embodiment, the reset voltage level of the processor 3 is 2.6 volts. The reset voltage level is given by the processor specifications. The processor 3 controls an insulin pump (not shown) to deliver insulin from a reservoir (not shown) to a patient in a substantially continuous way as discussed above.

The voltage supervisor 4 is connected to the output of the voltage converter 6 such that it can monitor the voltage VDD. If the voltage VDD drops to a response voltage level, for example 2.7 volts, the voltage supervisor 4 responds and generates an output signal indicative of this event. The output of the voltage supervisor 4 is connected to an input of the processor 3, preferably to an interrupt input port of the processor 3. An analog input of the processor 3 is connected to the battery 2 such that the battery voltage Vbat can be determined. In this configuration, the processor 3 includes an A/D converter which converts the analog voltage Vbat into a digital value which can be processed by the processor 3. As an alternative, the A/D converter can be external to the processor 3 as discussed above.

If the voltage supervisor 4 indicates that the voltage VDD has dropped to the response voltage level, for example 2.7 volts, the processor 3 starts sampling and logging the voltage Vbat and stores the values into memory 5 which is connected to the processor 3 either directly or via a link such as a data bus.

The medical infusion pump 1 is configured to test, during normal operation, the battery 2 as described above and to provide a warning or alert, such as a message on a device display, an audible and/or a tactile alert if the battery 2 approaches the end of its lifetime. A warning or alert may be provided at one or multiple levels of the voltage Vbat for which the voltage VDD is above the response voltage level as discussed above previously. While the response voltage level is generally selected below the specified output voltage level of the voltage converter 6, a warning or alert is favorably given during normal operation at a voltage level for which the specified output voltage of the voltage converter 6 is still maintained, thus allowing replacement of battery 2 in due time and especially prior to the voltage supervisor 4 responding.

The battery is checked automatically during normal operation in a time interval of typically some minutes. Those checks, however, require the processor to be in an operational mode and typically also involve coupling the battery to a test load. They are accordingly rather power consuming and should therefore not be carried out continuously or too frequently. Those checks do therefore typically not detect a sudden and unpredictable interruption of the power supply.

Figure 3:
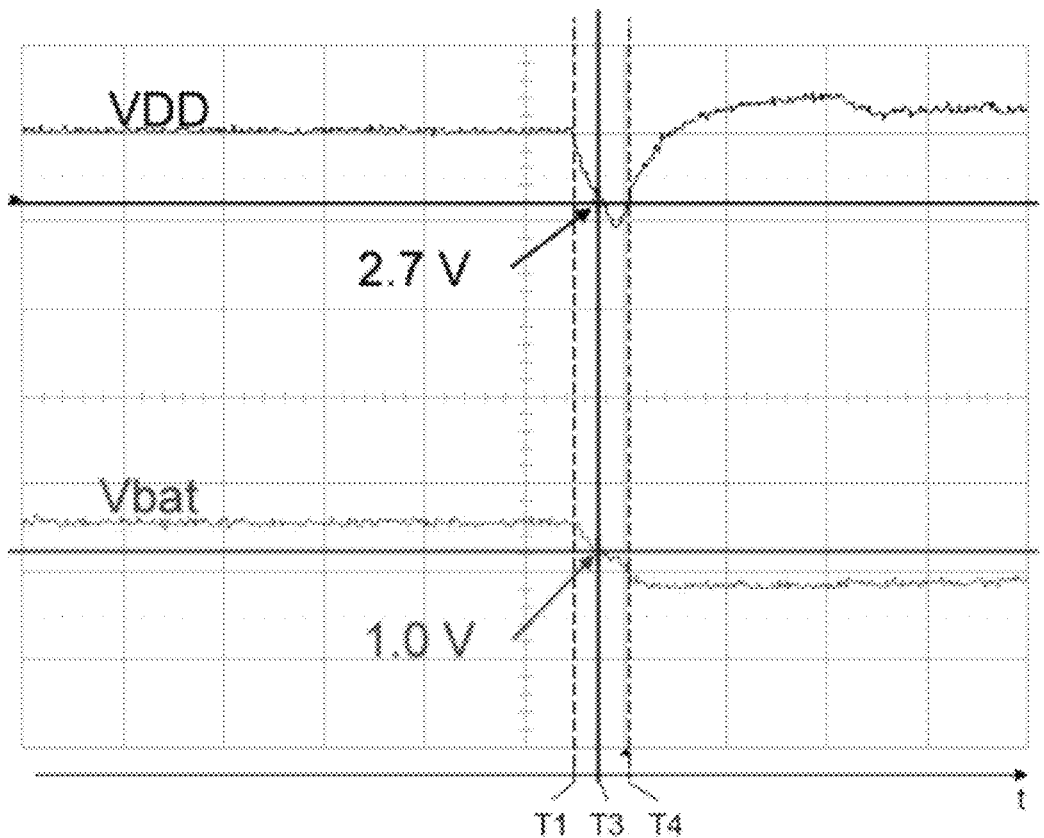
FIG. 3 depicts voltage level profiles for a weak battery.

The cause for the voltage VDD dropping to response voltage level can be one of several events. One event is that the battery 2 becomes weak. In this case, the internal resistance of the battery 2 causes a slight reduction of the voltage Vbat. An exemplary profile of voltage Vbat over time is depicted in FIG. 3. At a time T1, the voltage Vbat starts decreasing. About that time, the processor supply voltage VDD starts falling. At the time T3, the voltage VDD has fallen to a predetermined voltage level such that the voltage supervisor 4 responds and notifies the processor 3. Accordingly, the processor 3 starts logging the voltage Vbat in the memory 5. In the present example, the voltage Vbat falls from a nominal voltage of 1.3 volts to a reduced voltage of 0.9 volts and remains about that level.

The voltage converter 6 is able to stabilize the voltage VDD even from the reduced input voltage. As can be seen from FIG. 3, the voltage converter 6 can compensate the drop in the voltage Vbat. At the time T4, the voltage VDD rises above the predetermined voltage level of 2.7 volts again. At that time, the processor 3 stops logging Vbat. From the voltage Vbat being 0.9 volts at the time T4, it can be determined that the cause of the drop of the processor supply voltage VDD was within the battery 2, that is, the battery is of poor quality and has a high internal resistance.

Figure 2:
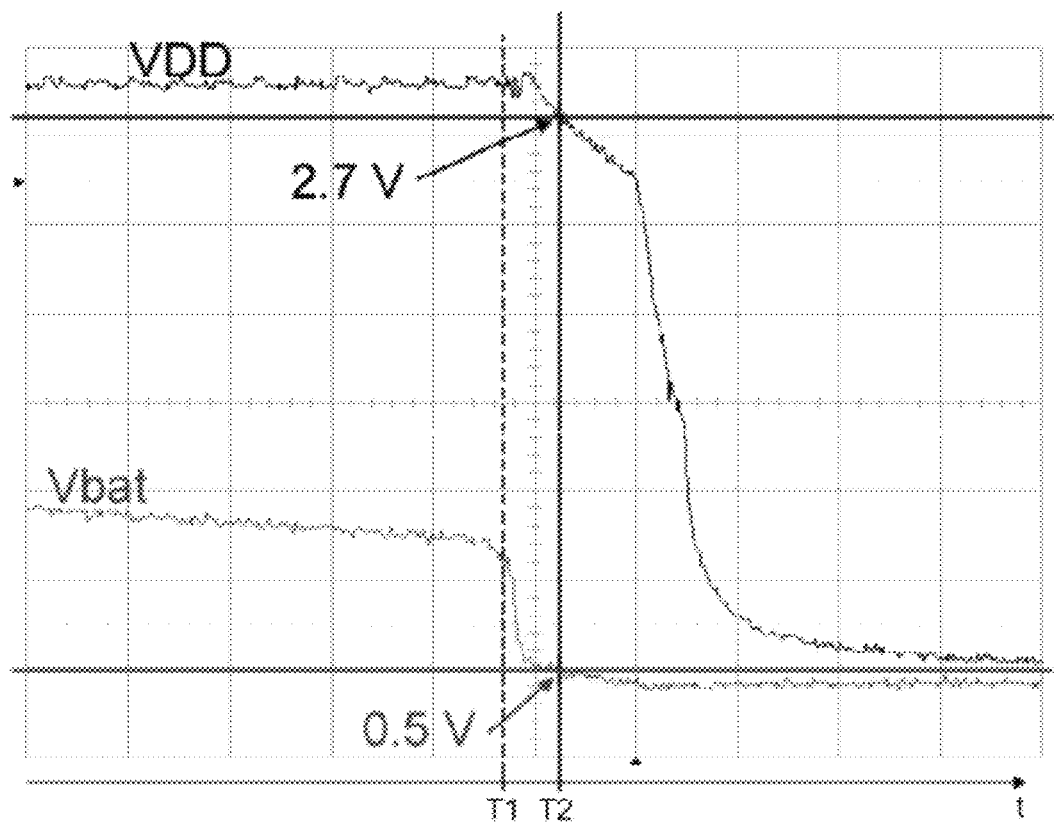
FIG. 2 depicts voltage level profiles when a power source is removed.

FIG. 2 shows the profiles of voltages Vbat and VDD for a second event in which the user of the infusion pump 1 removes the battery 2 during normal operation of the infusion pump. This kind of mishandling is known to occasionally occur if a user intends to replace the battery 2 but forgets to previously stop operation of the infusion pump by switching it into a different operational mode, for example, the stop mode or the maintenance mode, for replacing the battery. In this case, when the battery 2 is removed at a time T1, the voltage Vbat rapidly drops from the nominal value of 1.3 volts to a level of 0.5 volts. The 0.5 volts level results from an internal buffer capacitor (not shown) in the power supply path. In an unbuffered system, the voltage level would drop to zero. About that time T1, the voltage VDD starts decreasing. At a time T2, the voltage VDD has reached the response voltage level, 2.7 volts in the present example, such that the voltage supervisor 4 responds and notifies the processor 3.

The processor 3 then starts logging the battery voltage Vbat in the memory 5. Since the voltage converter 6 is not able to stabilize its output voltage VDD, it falls to and below the reset voltage level. The logging data are stored in the memory 5 where they are maintained, independent of the drop and/or interruption of the voltage Vbat and VDD, respectively.

From the logged voltage it can be seen by a retrospective analysis that the battery voltage was already low at the time when the logging was started, in particular considerably lower as in the case of a weak battery as discussed above with reference to FIG. 3. Therefore, it can be concluded that the battery was not present at that time, i.e., that a misuse has occurred by removing the battery with the device being in operation mode.

If a special mode, such as a stop mode or a maintenance mode, is provided and which should be selected for replacing the battery, monitoring of voltage VDD may not be carried out in that mode. Alternatively, it may be carried out such that voltage supervisor 4 responds when battery 2 is removed. For such embodiments, the voltage log may be cleared with the following power-up since it is not indicative of any mishandling, misuse, or battery or device error.

When the power supply of the infusion pump 1 is subsequently restored, the processor 3 powers up again and a corresponding entry is stored in a device history. The voltage log may be permanently kept in the memory and stored, or characteristic data may now be extracted or computed from the log and may be permanently stored, while the voltage log itself is cleared.

If the time between voltage VDD falling to the reset voltage of the processor 3 and the time at which the processor 3 is powered up again is longer than a predetermined time span, this indicates that the battery 2 was (temporarily) removed.

This time span can be determined as follows. When the processor and the infusion pump 1 are powered up again, they may run through a self-testing and powering-up routine of several seconds. The program code of the power-up routine is typically part of the general firmware code that controls operation of the processor 3. After completing the power-up routine, a corresponding power-up entry is stored in the history memory of the device together with a timestamp. If the time between the beginning of the logging, or the last logged value before voltage VDD has dropped to the reset voltage level, and the power-up entry is considerably longer than the time required for running through the power-up routine (i.e. in the range of half a second or more), the battery is viewed as having been removed. Otherwise, the time span would reflect that the battery would have been disconnected only for a very short period, e.g., because of a dropping of the device.

Figure 4:
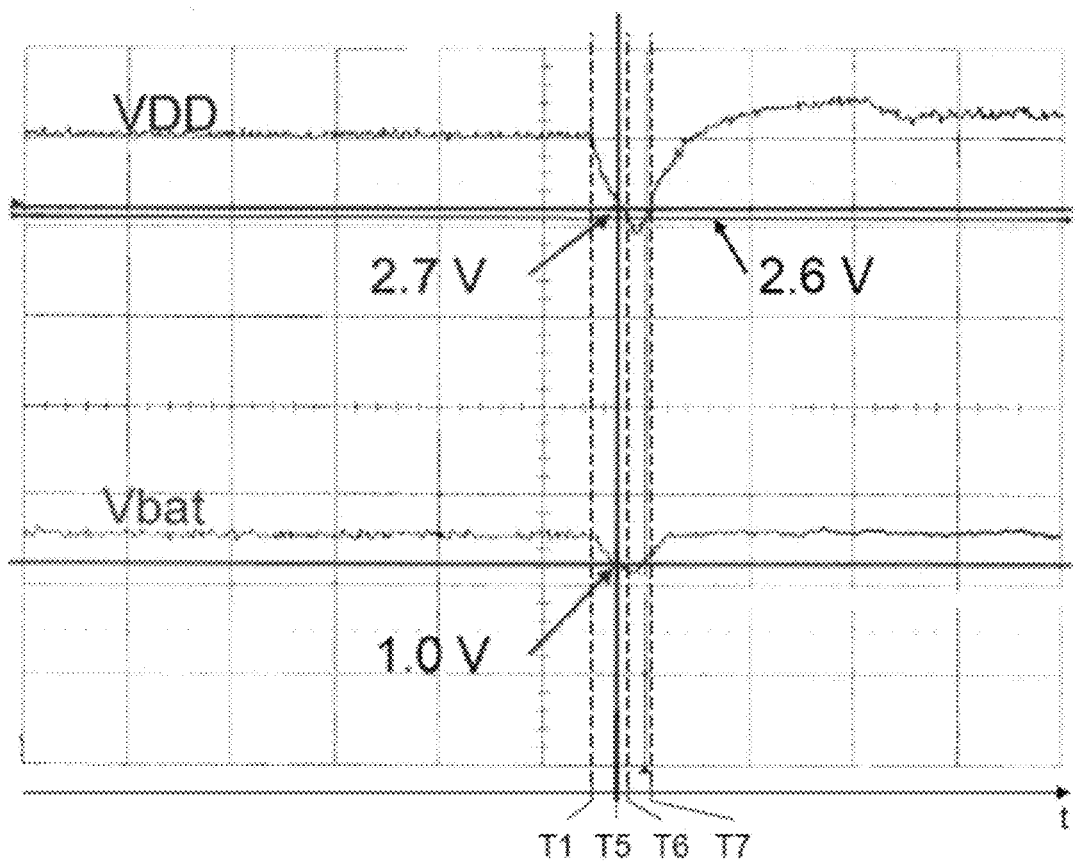
FIG. 4 depicts voltage level profiles for a dropped infusion pump.

In this latter case of dropping the infusion pump 1, the power supply of the infusion pump 1 may be interrupted only for a short period of time as shown in FIG. 4, such as, for example, when a contact spring which establishes the electrical contact with an electrode of the battery temporarily disconnects. In this example, the temporary disconnect causes the voltage VDD to drop sharply at a time T1 to the response voltage level at time T5. At time T6, the voltage VDD falls to the reset voltage level of the processor 3, as shown in FIG. 4, so that the processor 3 terminates operation and powers up again when the voltage VDD rises to the reset voltage again at time T7. After completing the power-up routine, a corresponding power-up entry is stored in the history memory 5 of the device. If the time between the beginning of the logging (or the last logged value before VDD has fallen to the reset voltage level and logging has stopped) and the power-up entry is only slightly longer (i.e. in the range of milliseconds or even microseconds) than the time required for powering up, then it is assumed that an interruption in the power supply was most likely caused by a drop of the infusion pump 1 since it is not possible for a user to physically remove and re-install the battery in that short time period.

However, the interruption of the power supply may be so short that the voltage VDD drops to the response voltage level, causing the voltage supervisor 4 to respond, but fails to drop to the reset voltage of the processor 3. In this case, operation of the infusion pump 1 is not impaired, and the corresponding event is accordingly a "near interruption". In contrast to the cases that where previously discussed, the logged voltage profile can be cleared and no permanent storing is required for a near interruption. This may be carried out by the device automatically after logging has stopped. As an alternative, the logged voltage profile can be permanently stored anyway for information purposes in this case. As discussed above, certain characteristic data, such as, for example, the voltage Vbat at the beginning of the logging, when the voltage VDD reaches the reset voltage level, the time span between beginning and ending of the logging, and the time span until the next following power-up, may be stored additionally or alternatively to the actual voltage profile.

A drop of the voltage Vbat, and therefore of the voltage VDD, can also occur if large currents are drawn from the battery 2 and the battery 2 is weak, but still capable of powering the infusion pump under typical operational conditions. This might be the case, for example, if the pump is activated to infuse an amount of insulin, for example to infuse an on-demand insulin bolus, while the background light of a typically present display is switched on. However, the background light and the pump are often activated for several seconds such that the voltage Vbat decreases slowly because of the drawn current. In this case, the time span between the beginning of the logging and the last logged value before the voltage VDD has dropped to the reset voltage level as well as the power-up entry will be quite long. In addition, it will be noted in the log that the voltage Vbat does not drop as deep as to zero or near zero. Therefore, power interruption caused by large power consumption in combination with a weak battery can be retrospectively identified and distinguished from a device mishandling.

Figure 5:
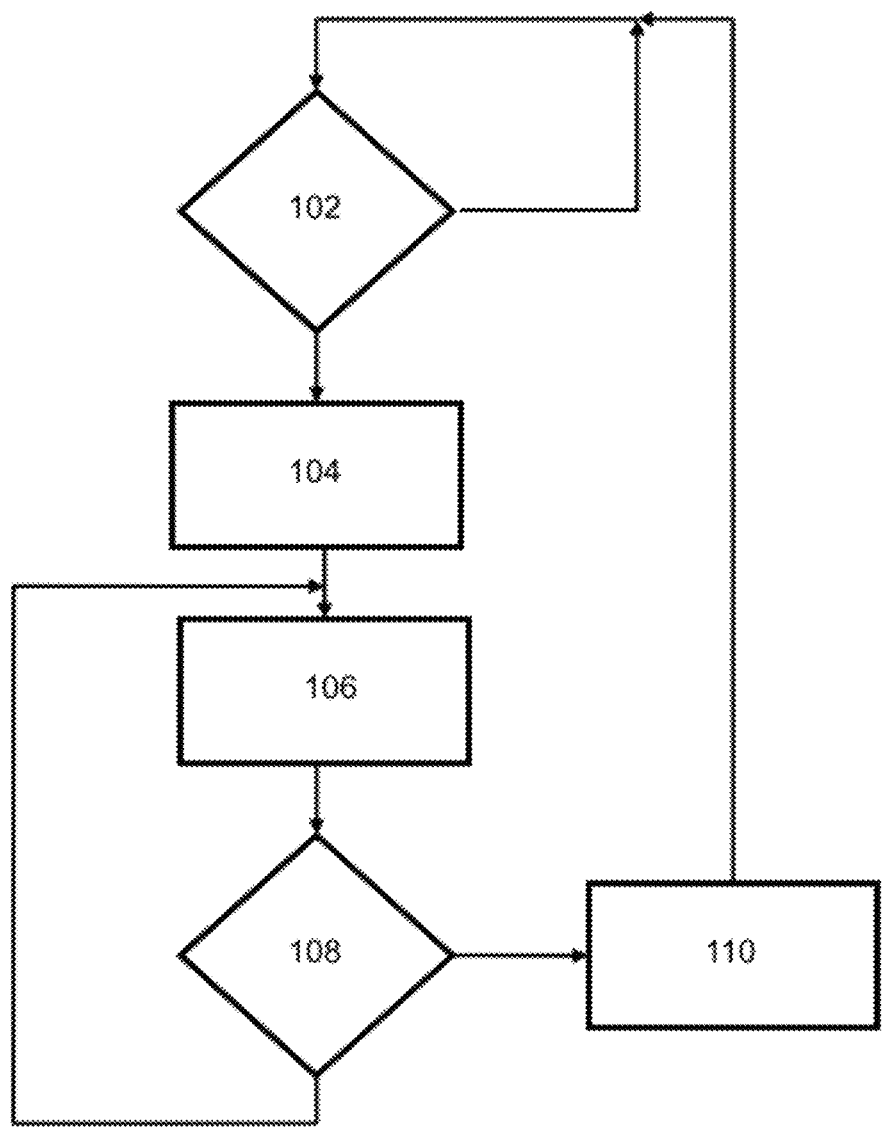
FIG. 5 depicts an exemplary operational flow diagram for logging the power source voltage according to an illustrated embodiment.

FIG. 5 schematically illustrates, in combination with FIG. 1, steps that may be carried out in an exemplary embodiment. In step 102, the voltage supervisor 4 monitors voltage VDD and checks whether it has dropped to the response voltage level. If this is not the case, logging is continued. Step 102 is carried out continuously during normal operation as described above. If voltage VDD has dropped to the response voltage level, the voltage supervisor 4 notifies, in step 104, the processor 3, e.g., via an interrupt line and the processor starts a logging routine, including activating an A/D converter. The following steps are carried out under the general control of processor 3. In step 106, a current value of voltage Vbat is logged, that is, A/D converted and stored in memory 5. Alternatively, as described above, an A/D converter may be operated continuously and may be checked in step 102 to detect if the voltage Vbat is to be logged. In step 108, it is tested whether logging may be stopped because the voltage VDD will not drop to the reset level according to a method as described above. In this case, operation is continued with step 110. In step 110, the logging routine is stopped. Also in step 110, the voltage log may optionally be cleared and/or a "nearly interruption" history entry may be made. Operation subsequently proceeds with the monitoring step 102.

If logging can not be stopped in step 108, operation continues with step 106 where a next value is logged. Logging continues until it is stopped according to the test in step 108 or the voltage VDD drops to the reset voltage level.

With the power supply being restored, that is, with the same or a new battery 2 being inserted again if it was removed or after contact is again established after a drop or mechanical shock, a power-up routine is run through as described above, including a corresponding history entry. When powering up infusion device following a power supply interruption as described, a special entry is favorably made in the history in addition or alternatively to the general power-up entry.

In embodiments where only characteristic data are stored rather than complete voltage logs, processor 3 may now extract or compute those data and store them in the history, followed by clearing the power log.

What has been described above are examples of the subject invention. It is, of course, not possible to describe every conceivable combination of components or methodologies, but one of ordinary skill in the art will recognize that many further combinations and permutations of the subject invention are possible. Accordingly, the subject invention is intended to embrace all such alterations, modifications and variations that fall within the spirit and scope of the claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method for logging a power source voltage (Vbat) of a power source in a medical infusion pump, the medical infusion pump comprising a processor, the power source powering the processor with the power source voltage (Vbat), the method comprising:
   detecting if a processor supply voltage (VDD) provided to the processor is interrupted;
   logging logged data comprising the power source voltage as a function of time starting when an interruption occurs;
   maintaining the logged data while the power source is interrupted;
   storing the logged data to enable a retrospective analysis of the logged data; and
   determining a cause of the voltage interruption based at least in part on an analysis of the logged data.

2. The method of claim 1, wherein the analysis of the logged data is performed by a person.

3. The method of claim 1, wherein the analysis of the logged data is performed by an automated system.

4. The method of claim 1, wherein the analysis of the logged data is performed by the medical infusion pump.

5. The method of claim 4, wherein the medical infusion pump displays a result of the analysis.

6. The method of claim 1, wherein the analysis of the logged data is performed following a subsequent power-up.

7. The method of claim 1, wherein the medical infusion pump stores the logged data.

8. The method of claim 1, wherein the medical infusion pump permanently stores characteristic data that is extracted from the logged data.

9. The method of claim 1, further comprising comparing the logged data with one or more characteristic reference profiles.

10. The method of claim 9, wherein the characteristic reference profiles are visually analyzed by a person.

11. The method of claim 9, wherein the characteristic reference profiles are automatically analyzed by a computing device.

12. The method of claim 1, wherein the detecting if the processor supply voltage (VDD) provided to the processor is interrupted occurs via detecting if the processor supply voltage (VDD) drops to a predetermined response voltage level which is higher than a reset voltage level of the processor.

13. The method of claim 12, wherein the logging the logged data occurs when the processor supply voltage (VDD) has dropped to the predetermined voltage level.

14. The method of claim 1, further comprises transmitting the logged data to an external computing device when the power supply provided by the power source is interrupted to enable a retrospective analysis.

15. The method of claim 14, further comprises utilizing as the external computing device a dedicated diagnosis device comprising a data interface.

16. The method of claim 15, further comprises utilizing as the data interface an infrared interface.

17. The method of claim 15, further comprises utilizing as the data interface a radio frequency interface.

18. The method of claim 15, further comprises controlling the medical infusion pump during normal operation via the data interface.

19. The method of claim 1, further comprises detecting if the processor supply voltage (VDD) ceases to be interrupted; and recalling the logged data from a first time approximately occurring when the processor supply voltage is interrupted to a second time approximately occurring when the processor supply voltage ceases to be interrupted, wherein the determining of the cause of the voltage interruption is determined via comparing the recalled logged data with one or more characteristic reference profiles.

20. The method of claim 19, further comprises performing the comparing of the recalled logged data with the one or more characteristic reference profiles manually or automatically.

* * * * *

UNITED STATES PATENT AND TRADEMARK OFFICE
CERTIFICATE OF CORRECTION

PATENT NO. : 8,670,836 B2  
APPLICATION NO. : 13/570696  
DATED : March 11, 2014  
INVENTOR(S) : Reto Aeschlimann et al.

Page 1 of 1

It is certified that error appears in the above-identified patent and that said Letters Patent is hereby corrected as shown below:

In the Claims

Col. 16, Line 41, Claim 19, "and recalling the" should read --and evaluating the--;

Col. 16, Line 46, Claim 19, "via comparing the recalled logged data" should read --via comparing the logged data--; and Col. 16, Line 21, Claim 20, "comparing of the recalled logged data" should read --comparing of the logged data--.

Signed and Sealed this  
Eleventh Day of November, 2014

Michelle K. Lee  
*Deputy Director of the United States Patent and Trademark Office*

UNITED STATES PATENT AND TRADEMARK OFFICE
CERTIFICATE OF CORRECTION

Page 1 of 1

PATENT NO. : 8,670,836 B2
APPLICATION NO. : 13/570696
DATED : March 11, 2014
INVENTOR(S) : Reto Aeschlimann et al.

It is certified that error appears in the above-identified patent and that said Letters Patent is hereby corrected as shown below:

In the Claims

Col. 16, Line 41, Claim 19, "and recalling the" should read --and evaluating the--;

Col. 16, Line 46, Claim 19, "via comparing the recalled logged data" should read --via comparing the logged data--; and Col. 16, Line 49, Claim 20, "comparing of the recalled logged data" should read --comparing of the logged data--.

This certificate supersedes the Certificate of Correction issued November 11, 2014.

Signed and Sealed this
Ninth Day of December, 2014

Michelle K. Lee
*Deputy Director of the United States Patent and Trademark Office*